United States Patent
Kwon et al.

(10) Patent No.: US 11,642,054 B2
(45) Date of Patent: May 9, 2023

(54) WIRE-ASSEMBLY APPARATUS FOR INVASIVE BIOSENSORS

(71) Applicant: DexCom, Inc., San Diego, CA (US)

(72) Inventors: Ohseung Kwon, Sunnyvale, CA (US); Xianyan Wang, San Jose, CA (US); Timothy Stowe, Mountain View, CA (US)

(73) Assignee: DexCom, Inc., San Diego, CA (US)

( * ) Notice: Subject to any disclaimer, the term of this patent is extended or adjusted under 35 U.S.C. 154(b) by 322 days.

(21) Appl. No.: 16/890,901

(22) Filed: Jun. 2, 2020

(65) Prior Publication Data

US 2020/0297254 A1 Sep. 24, 2020

Related U.S. Application Data

(63) Continuation of application No. 15/362,944, filed on Nov. 29, 2016, now Pat. No. 10,702,198.

(51) Int. Cl.
*A61B 5/145* (2006.01)
*A61B 5/1473* (2006.01)
*A61B 5/00* (2006.01)

(52) U.S. Cl.
CPC .......... *A61B 5/1473* (2013.01); *A61B 5/1451* (2013.01); *A61B 5/14532* (2013.01); *A61B 5/14735* (2013.01); *A61B 5/6833* (2013.01); *A61B 2562/125* (2013.01)

(58) Field of Classification Search
CPC ..... A61B 5/1473; A61B 5/145; A61B 5/6833; A61B 5/14735; A61B 5/1451; A61B 5/14532; A61B 2562/125
See application file for complete search history.

(56) References Cited

U.S. PATENT DOCUMENTS

| | | | |
|---|---|---|---|
| 6,157,543 A | 12/2000 | Ashdown et al. | |
| 7,344,409 B2 | 3/2008 | Lang et al. | |
| 9,007,781 B2 | 4/2015 | Moein et al. | |
| 2002/0004980 A1 | 6/2002 | Onitsuka et al. | |
| 2010/0198034 A1* | 8/2010 | Thomas | A61B 5/6849 600/365 |
| 2011/0290645 A1 | 12/2011 | Brister et al. | |
| 2015/0351689 A1* | 12/2015 | Adams | A61B 5/6833 600/300 |
| 2016/0026910 A1* | 1/2016 | Ayala | G06K 19/07773 235/492 |

(Continued)

FOREIGN PATENT DOCUMENTS

JP S6122686 A 1/1986

OTHER PUBLICATIONS

European Extended Search Report dated May 6, 2020 for Application No. 17877175.4; 9 pages.

(Continued)

*Primary Examiner* — Eric J Messersmith
(74) *Attorney, Agent, or Firm* — Snell & Wilmer, LLP

(57) ABSTRACT

In some aspects, an apparatus for a biosensor includes a sensor wire and a rigid member. The rigid member may be coupled to the sensor wire and include a contact surface. The contact surface may be sized to enable a suction head of a robotic placement device to create a vacuum seal on the contact surface for lifting the sensor wire and rigid member.

23 Claims, 4 Drawing Sheets

(56) References Cited

U.S. PATENT DOCUMENTS

2016/0157765 A1* 6/2016 Zhu ........................ C08L 83/04
                                                              524/588
2017/0290512 A1* 10/2017 Antonio ........... A61B 5/150633
2018/0146894 A1   5/2018 Kwon et al.
2018/0263543 A1*  9/2018 Harttig ............... A61B 5/14532

OTHER PUBLICATIONS

International Search Report and Written Opinion dated Dec. 17, 2017 for Application No. PCT/US2017/054106; 6 pages.
International Search Report and Written opinion for Application No. PCT/US2017/054106 dated Dec. 21, 2017, 5 pages.

\* cited by examiner

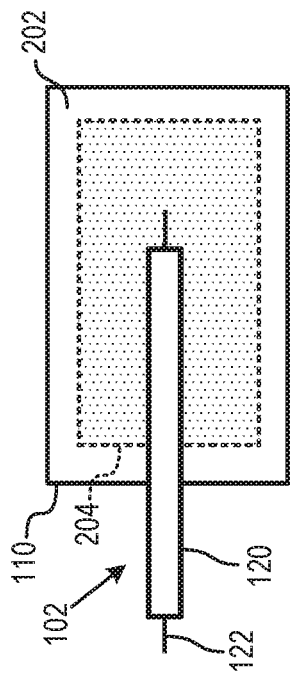
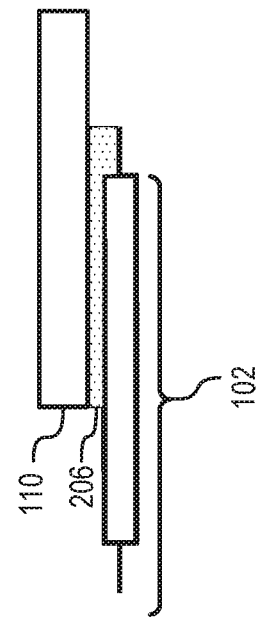
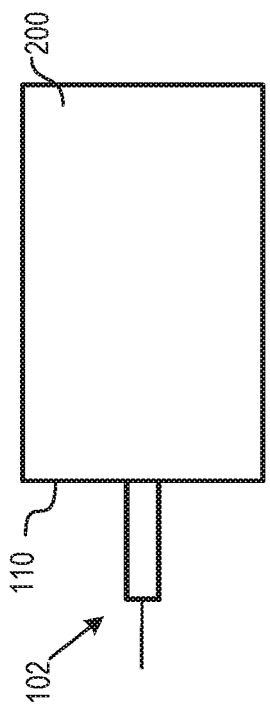
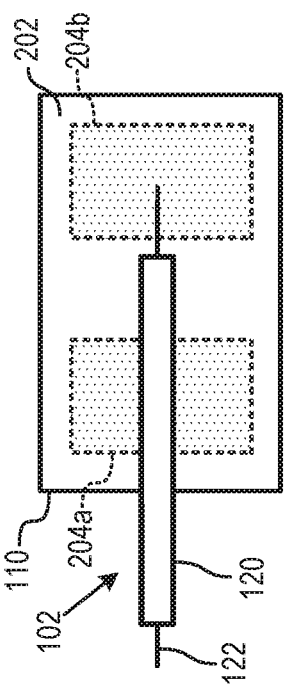
FIG. 2A
FIG. 2B
FIG. 2C
FIG. 2D

WIRE-ASSEMBLY APPARATUS FOR INVASIVE BIOSENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/362,944, filed Nov. 29, 2016. The aforementioned application is incorporated by reference herein in its entirety, and is hereby expressly made a part of this specification.

FIELD

The present disclosure generally relates to invasive biosensors and more specifically to an apparatus for assembling wires for invasive biosensors.

BACKGROUND

Invasive biosensors, such as sensors for wearable glucose monitoring devices, include thin wires that are insertable into a patient's skin. Sensing circuitry reads biological information about the patient via the thin wires. Once an invasive biosensor is inserted into a patient's skin, the electrical connections between the wires and circuitry remain exposed to potential moisture that may significantly affect the biosensor performance. For example, many electrochemical-based sensors may have performance impacts relating to calibration offsets or increases in the noise floor level due to moisture-caused current leakage within the electronics enclosure. The impact is particularly high for biosensors included in wearable devices that may be exposed to perspiration on the patient's skin, weather, and other sources of moisture typically experienced by human skin. In addition to this consideration, the size of the device is always a practical consideration for wearables. To accommodate the required sensing circuitry, power source, and the like to process the biological information, wearable glucose monitoring devices may include multiple parts that are connected together to form working devices. Not only does the use of multiple parts cause the devices to be bulky, but it also creates multiple areas for possible moisture ingress (e.g., seals between parts).

SUMMARY

Various examples are described for apparatuses to assemble sensor wires for invasive biosensors. For example, one disclosed apparatus for a biosensor includes a sensor wire and a rigid member. The rigid member is attached to the sensor wire and includes a contact surface. The contact surface is sized to enable a suction head of a robotic placement device to create a vacuum seal on the contact surface for lifting the sensor wire and rigid member.

Another disclosed device includes a wearable monitoring device including a printed circuit board disposable in a housing having a planar surface for positioning the wearable monitoring device on a patient's skin. The device also includes a sensor wire including one or more electrodes electrically coupled, at a connection point on a printed circuit board, to circuitry disposed on the printed circuit board. The sensor wire includes distal end that is insertable into the patient's skin. The device also includes a rigid member connected to the printed circuit board and the sensor wire. The rigid member is positioned on the printed circuit board such that the connection point is between the printed circuit board and a coupling surface of the rigid member. The rigid member includes a contact surface opposite the coupling surface. The contact surface is sized to enable a suction head of a robotic placement device to create a vacuum seal on the contact surface for positioning the rigid member on the printed circuit board.

One disclosed method for assembling a biosensor includes receiving a sensor wire and a rigid member. The sensor wire includes a distal end for insertion into a patient's skin and a proximal end connected to the rigid member. The method also includes creating, by a suction head of a robotic placement device, a vacuum seal on a surface of the rigid member for grasping the rigid member. The method also includes positioning, by the robotic placement device and using the vacuum seal, the sensor wire and the rigid member on a printed circuit board. The method also includes applying, by the robotic placement device, a force on the rigid member in a direction of the printed circuit board to cause a pressure-sensitive adhesive between the rigid member and the printed circuit board to bond the rigid member to the printed circuit board.

A further disclosed device includes a glucose monitoring system including a sensor wire having a first portion injectable into a patient's skin. The first portion includes means for generating glucose information. The glucose monitoring system also includes positioning means for enabling a suction head of a robotic placement device to position the sensor wire on a printed circuit board and electronically couple the sensor wire to circuitry disposed on the printed circuit board for determining a glucose level for the patient. The positioning means is physically coupled to the sensor wire to enable the robotic placement device to lift the positioning means and the sensor wire.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 2A through 2D show different cross-sectional views of an example wire-assembly apparatus according to some aspects of the present disclosure.

DETAILED DESCRIPTION

Examples are described herein in the context of sensor wire assemblies for invasive biosensors. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Figure 1:
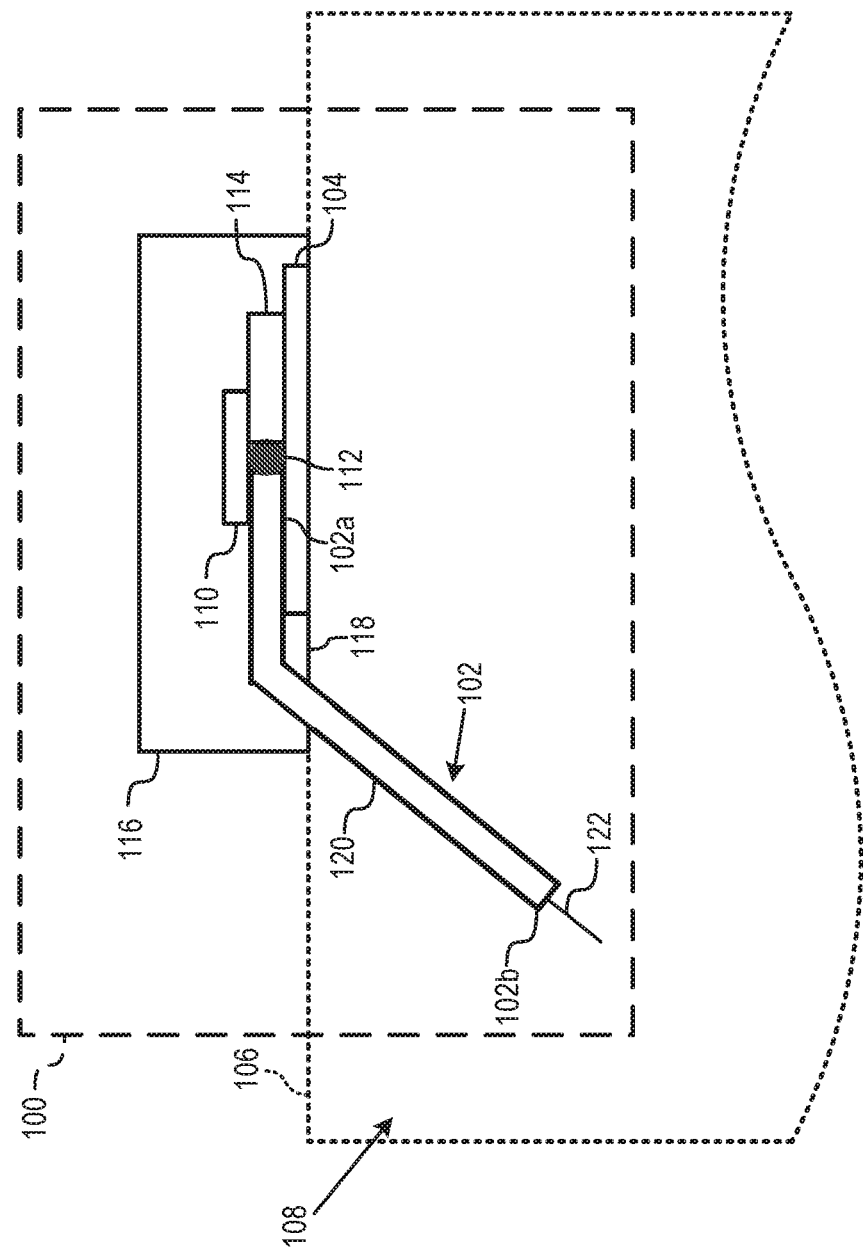
FIG. 1 shows a side, cross-sectional view of an illustrative example of an invasive biosensor including a wire-assembly apparatus according to some aspects of the present disclosure.

Illustrative Example of an Invasive Biosensor Including a Wire Assembly Apparatus One example invasive sensor shown in FIG. 1 is a biosensor 100, such as a glucose sensor. The biosensor 100 includes a sensor wire 102 including a proximal end 102a that is electrically coupled to a printed circuit board ("PCB") 104. A distal end 102b of the sensor wire 102 is injected into a patient's skin 106 to measure biological parameters (e.g., glucose levels) in the interstitial fluid of subcutaneous tissue 108 beneath the skin 106. Although the skin 106 is depicted in FIG. 1, the skin 106 is not a part of the biosensor 100, as indicated by the dashed lines. The sensor wire 102 may also be physically coupled to a rigid member 110 or other positioning means for enabling the sensor wire 102 to be picked up and positioned in a desired location during assembly of the biosensor 100.

During assembly of the biosensor 100, the rigid member 110 provides a contact surface that enables the sensor wire 102 to be lifted by a suction head of a robotic placement device, such as a pick-and-place tool or machine, and positioned on the PCB 104. For example, the sensor wire 102's outer diameter may be large enough to transmit electrical signals from the interstitial fluid to the PCB 104, but too small to be grasped by the robotic placement device. A surface of the rigid member 110 is therefore adhered to the sensor wire 102 to enable the robotic placement device to pick both the rigid member 110 and the sensor wire 102 for placement on the PCB 104.

The sensor wire 102 is positioned on the PCB 104 to electrically couple to sensing circuitry 114 on the PCB 104. The rigid member 110 is positioned to cover a connection point 112 between the sensor wire 102 and the sensing circuitry 114. In some aspects, the connection point 112 is a conductive pad on the PCB 104 at which the sensor wire 102 is electronically coupled to the sensing circuitry 114. In some aspects, the sensor wire 102 and the sensing circuitry 114 are physically connected at the connection point 112. In additional and alternative aspects, the sensor wire 102 and the sensing circuitry 114 are physically separate, but electrically coupled through one or more connection paths of the connection point 112. Although not shown in FIG. 1, potting material may be injected around the rigid member 110 to provide a moisture barrier for the connection point 112. Non-limiting examples of the potting material include epoxy, silicone, acrylic, polyurethane, or other means for providing a moisture barrier to the connection point 112

In some aspects, the sensing circuitry 114 includes a processing device and a computer-readable medium, such as a memory chip, read-only memory ("ROM"), random access memory ("RAM"), or an application-specific integrated circuit ("ASIC"), coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from the electrodes 120, 122. The PCB 104 and the sensing circuitry 114 are disposed in a housing 116 of the biosensor 100. The housing 116 may be compact in size for placing on the skin 106. The housing 116 includes a surface 118 having a substantially planar surface. In various cases, the substantially planar shape enables the biosensor 100 to be placed on the skin 106. Although the housing 116 is shown in FIG. 1 as having a rectangular cross-sectional shape, the housing 116 may include other cross-sectional shapes that serve the same functions as described herein. The housing 116 may be made of any suitable material for housing the biosensor 100. Non-limiting examples of materials that may be suitable for the housing 116 include polyethylene, polyvinyl chloride ("PVC"), polypropylene, nylon, polyurethane, polycarbonate, steel, aluminum, and other plastics and metals. The biosensor 100 may be secured to the skin 106 using an adhesive, band, strap, or other securing means. In some aspects, the biosensor 100 is worn for extended period of time (e.g., days, weeks, months, etc.). The sensor wire 102 may include a length of substantially between 5 millimeters to 25 millimeters. In various cases, the sensor wire 102's length within the specified range enables the sensor wire 102 to extend from beneath the skin 106 to the sensing circuitry 114 with allowance for the patient's movement. In one example, the sensor wire 102 includes an outer diameter, with coating, of approximately 170 microns for the electrode 120 and an outer diameter of approximately 100 microns for the electrode 122. In additional examples, the sensor wire 102 generally has a maximum outer diameter approximately between 100 microns and 300 microns. The sensor wire 102's thickness, or gauge, within the specified ranges may be selected to enable the sensor wire 102 to remain injected into the skin 106 during this period with minimal discomfort.

The sensor wire 102 extends from the PCB 104 to the skin 106 through the housing 116. The sensor wire 102 may include one or more electrodes, chemicals, or other means for generating biological information. In this example, the sensor wire 102 includes two electrodes 120, 122 that are inserted into the skin 106 to expose the electrodes 120, 122 to the interstitial fluid in the subcutaneous tissue 108. Electrode 122 includes at least a portion of the sensor wire 102 having a platinum or platinum coating and electrode 120 includes a silver/silver-chloride (Ag/AgCl) material that covers a part of electrode 120. The electrode 122's platinum material is inert to prevent corrosion and may act as a catalyst for a reaction of proton reduction. The electrode 120's silver/silver-chloride material may cause a reaction between the silver material and the silver-chloride material to enable high current to pass through the electrode 120. In some aspects, a reactive material, such as glucose oxidase ("GOX"), is also coated on the electrode 122 to create reaction products with glucose present in the interstitial fluid. When a voltage is applied to the electrodes 120, 122, an electrical current is generated based on the amount of these reaction products generated by the glucose/GOX reaction. The electrical current is routed through the sensor wire 102 to the sensing circuitry 114. The sensing circuitry 114 may use the strength of the current to determine the patient's glucose levels. Although glucose level measurements are described in this example, the biosensor 100 may be configured to measure other biological parameters without departing from the scope of the present disclosure. Similarly, while the chemical materials applied onto the sensor wire 102 to form the electrodes 120, 122 and the reactive material coated onto the electrodes 120, 122 may be suitable for a glucose sensor, other material may be used according to other examples, based on the application of the biosensor 100.

This illustrative example is given to introduce the reader to the general subject matter discussed herein and the disclosure is not limited to this example. The following sections describe various additional non-limiting examples and examples of systems and methods for wire assemblies for invasive biosensors.

Turning now to FIGS. 2A through 2D, FIG. 2A shows a cross-sectional top view of the sensor wire 102 and the rigid member 110 prior to its assembly on the PCB 104 of FIG. 1. The rigid member 110 is attached to the sensor wire 102 to enable a robotic placement device to pick up, or otherwise lift the sensor wire 102 through the rigid member 110. For example, the rigid member 110 includes a contact surface 200 that the robotic placement device may use to pick up the rigid member 110. In some aspects, the contact surface 200 includes a substantially planar or smooth surface. In various cases, the substantially planar or smooth surface enables a suction head of the robotic placement device grip the contact surface 200 and form a vacuum seal on the rigid member 110. The suction head may create the vacuum seal by contacting the contact surface 200 and creating a suction force to form a seal that couples the suction head to the contact surface 200. The suction force created by the suction head may be strong enough to enable the robotic placement device to lift the rigid member 110 using the vacuum seal. In other aspects, the contact surface 200 may include a protrusion, depression, or may be otherwise shaped to correspond to the suction head's shape to enable the suction head to form the vacuum seal. The rigid member 110's minimum size may be dependent on the suction head's size, but may be large enough to enable the suction head to form the vacuum seal on the contact surface 200. The rigid member 110's maximum size may be dependent on the PCB 104's size. For example, in some aspects, the rigid member 110 is small enough to cover only the PCB 104's electrical connections at the connection point 112. In another example, the rigid member 110 is large enough to cover an entire surface of the PCB 104. In some aspects, the rigid member 110 includes a side or diameter length between approximately one millimeter and 10 millimeters. In additional aspects, the rigid member 110 is proportional to the sensor wire 102 length, such as a side measuring half the length of the sensor wire 102, or less. The contact surface 200 in FIG. 2A is shown as spanning the rigid member 110's entire surface, though the contact surface 200 may include only a portion of the surface without departing from the scope of the present disclosure. Similarly, though the rigid member 110 is shown as having a rectangular cross-section, the rigid member 110 may have any shape that provides a sufficient contact surface 200 for forming the vacuum seal to lift the rigid member 110 and the sensor wire 102 together.

The rigid member 110 has a rigidity to enable the suction head to create a sufficient vacuum seal for lifting the rigid member 110 and the sensor wire 102 in a controlled manner. For example, the rigid member 110 is rigid such that the rigid member does not deform in response to the suction force applied on the contact surface 200 by the suction head. The rigid member 110's stability in response to the suction force may enable the suction head to maintain control of the sensor wire 102's orientation to precisely position the sensor wire 102 and the rigid member 110 on the PCB 104. The rigid member 110's rigidity may depend on one or both of the rigid member 110's thickness and the material forming the rigid member 110. For example, the rigid member 110's thickness may be inversely proportional to the density of the material (e.g., a denser material may be used for a thinner rigid member 110 while a less dense material may necessitate a thicker rigid member 110). Non-limiting examples of material that may be used for the rigid member 110 include polycarbonate, polyurethane, polyvinyl chloride, or other suitable materials. In some aspects, the material is non-conductive to electrically isolate the electrical connections at the connection point 112.

FIGS. 2B and 2C show a cross-sectional bottom view of the sensor wire 102 and the rigid member 110. The sensor wire 102 is adhered to a coupling surface 202 positioned on a side of the rigid member 110 opposite the contact surface 200. The coupling surface 202 includes means for coupling the rigid member 110 to the PCB 104. For example, in FIG. 2B, adhesive 204 may bond the rigid member 110 to the PCB 104. The adhesive 204 may be positioned on the coupling surface 202 proximate to the sensor wire 102. Non-limiting examples of adhesives 204 include epoxy, glue, and other means for bonding the rigid member 110 onto the PCB 104. In some aspects, the adhesive 204 is pressure-sensitive adhesive to activate in response to a pressure force applied to the rigid member 110. For example, the adhesive 204 may be activated to form a bond with the PCB 104 in response to the robotic placement device applying a force on the contact surface 200 while positioning the rigid member 110 onto the PCB 104. In some aspects, the adhesive 204 is contiguously applied on the coupling surface 202 to bond both of the electrodes 120, 122 to the rigid member 110 as shown in FIG. 2B. In other aspects, the adhesive may be applied in separate applications 204a, 204b to individually bond the electrodes 120, 122, respectively, to the rigid member 110 as shown in FIG. 2C.

In some aspects, the adhesive 204 is non-conductive to prevent the adhesive from shorting the electrical connections of the sensing circuitry 114. In additional aspects, the adhesive 204 includes a conductive material that is intentionally positioned to enable additional connections of the sensing circuitry 114. For example, the adhesive 204 may be positioned on the rigid member 110 to provide a connection point between two components in the sensing circuitry 114 when the rigid member 110 is bonded to the PCB 104. In further aspects, the adhesive 204 may include one or more types of adhesive (e.g., a non-conductive material and a conductive material). The adhesive 204 may be pre-laminated, or otherwise pre-applied, onto the rigid member 110 or applied to the rigid member 110 during assembly of the biosensor 100. Although the adhesive 204 is shown in FIGS. 2B and 2C as positioned on the rigid member 110 prior to being installed on the PCB 1 prior to being installed on the PCB 104, the adhesive may 204 alternatively, or additionally, be positioned on the PCB 104 prior to installation.

FIG. 2D shows a cross-sectional side view of the sensor wire 102 and the rigid member 110. Means for coupling the sensor wire 102 and the rigid member 110, such as adhesive 206, may be included between the sensor wire 102 and the rigid member 110. In some aspects, the adhesive 206 is of the same or similar type as the adhesive 204. The adhesives 204, 206 may include non-toxic materials to enable the biosensor 100 to be wearable on the skin without risk of irritation or other damage to the patient. Although the adhesives 204, 206 are described as separate adhesives, in some aspects, the adhesives 204, 206 is the same adhesive. For example, the adhesives 204, 206 may include a pressure-sensitive adhesive. The sensor wire 102 may be pressed against the coupling surface 202 to activate the contacted portion of the adhesives 204, 206 and to bond the sensor wire 102 to the rigid member 110. The remaining adhesives 204, 206 may remain inactive until a pressure is applied to the rigid member 110 to adhere the rigid member 110 to the PCB 104.

Figure 3:
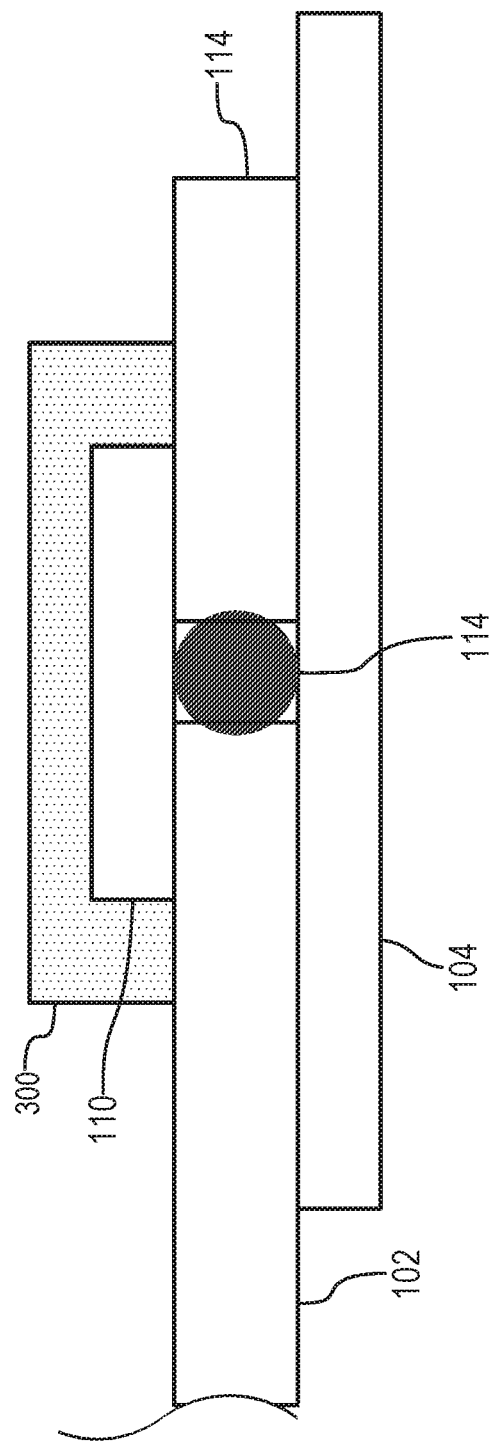
FIG. 3 shows a side, cross-sectional view of an example of a potted wire-assembly apparatus according to some aspects of the present disclosure.

FIG. 3 shows a zoomed in view of the biosensor 100 of FIG. 1 proximate to the connection point 112 between the sensor wire 102 and the sensing circuitry 114. The rigid member 110 is positioned on the PCB 104 such that the connection point 112 is between the rigid member 110 and the PCB 104. In some aspects, a potting material 300 is positioned proximate to the rigid member 110 as shown in FIG. 3. For example, the potting material 300 may be injected on top of and around the rigid member 110 to pot the rigid member 110 to the PCB 104. In some aspects, the potting material 300 includes a non-conductive material to prevent a short in the electrical connections at the connection point 112. The potting material 300 may provide a moisture barrier for the electrical connections on the PCB 104 at the connection point 112. Although the potting material 300 is shown as positioned only proximate to the rigid member 110, the potting material 300 may be applied to coat the components across the entire surface of the PCB 104.

Figure 4:
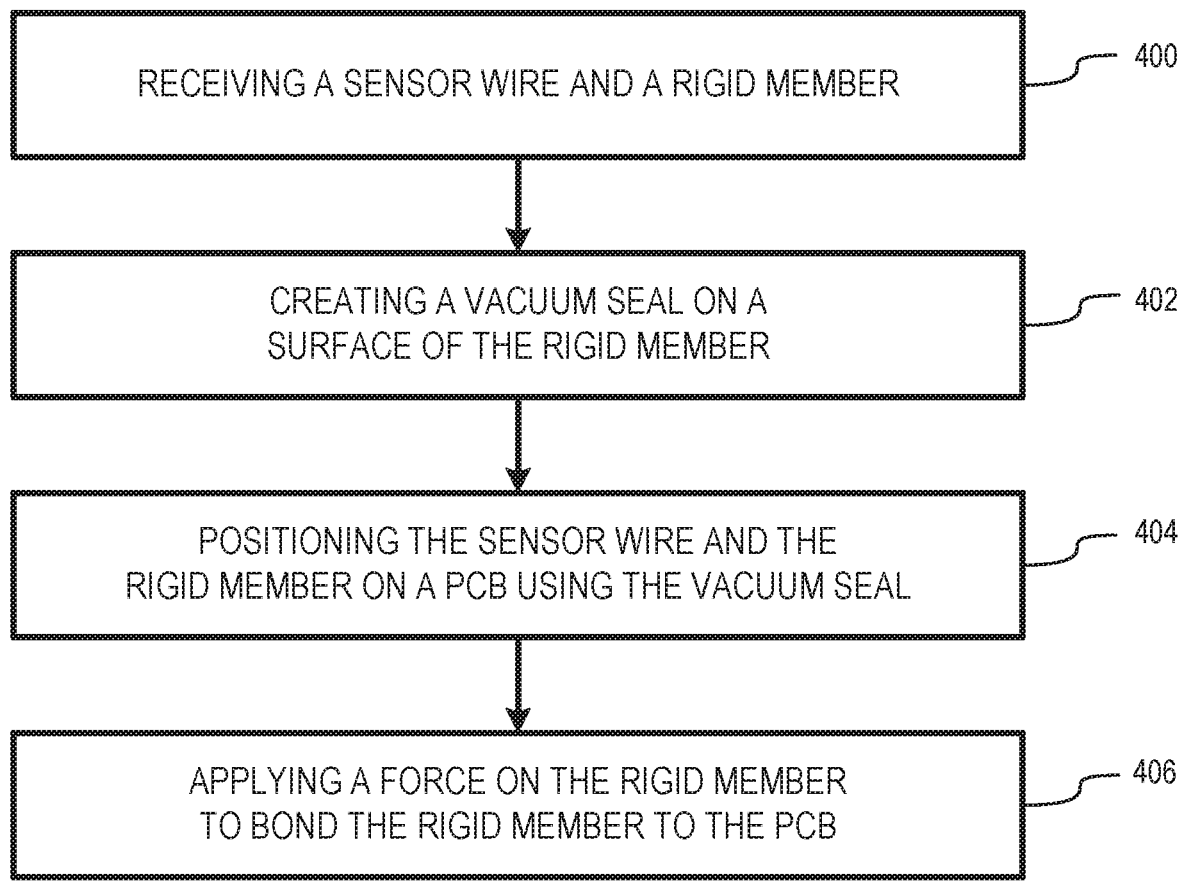
FIG. 4 shows an example method of assembling a biosensor with a wire-assembly apparatus according to some aspects of the present disclosure.

FIG. 4 is a flow chart of a process for assembling the biosensor 100. The process is described with respect to FIGS. 1-3, though other implementations are possible without departing from the scope of the present disclosure.

In block 400, the sensor wire 102 and the rigid member 110 are received. The sensor wire 102 and the rigid member 110 may be received by a robotic placement device, e.g., on an assembly line. In some aspects, the sensor wire 102 and the rigid member 110 are received as a single assembly with the sensor wire 102 and the rigid member 110 attached by the adhesive 206. In other aspects, the sensor wire 102 and the rigid member 110 are received separately and the adhesive 206 may be subsequently applied to the sensor wire 102 or the rigid member 110 to connect the sensor wire 102 and the rigid member 110. The sensor wire 102 may include one or more chemicals operable as the electrodes 120, 122. The sensor wire 102 may also include additional chemicals, such as a reactive material (e.g., glucose oxidase) to react with interstitial fluid beneath the skin 106. In some aspects, the chemicals forming the electrodes 120, 122 and the reactive material are pre-applied to the sensor wire 102 prior to being received by the robotic placement device. In other aspects, the sensor wire 102 may be received as a bare wire and the chemicals may be subsequently applied during the assembly of the biosensor 100. The rigid member 110 may include the adhesive 204 on the coupling surface 202. In some aspects, the rigid member 110 is received with the adhesive 204 pre-applied to the coupling surface 202. In other aspects, the adhesive 204 is applied subsequent to the rigid member 110 being received. In further aspects, the adhesive 204 is pressure-sensitive.

In block 402, a vacuum seal is created on the contact surface 200 of the rigid member. The vacuum seal may be created between a suction head of a robotic placement device and the contact surface. The suction head may apply a suction force on the contact surface 200 to form a seal that adheres the suction head to the suction head.

In block 404, the sensor wire 102 and the rigid member 110 are positioned on the PCB 104 using the vacuum seal. For example, the robotic placement device may maintain the suction force on the contact surface 200 as the robotic placement device moves the rigid member 110 and the sensor wire 102 to, and positions them on, the PCB 104. The robotic placement device may position the sensor wire 102 on the PCB 104 such that the proximal end 102a is placed to electronically couple with the sensing circuitry 114 on the PCB 104 at the connection point 112. In some aspects, the sensor wire 102 is positioned on the PCB 104 prior to the sensing circuitry 114 being positioned on the PCB 104. In other aspects, the sensing circuitry 112 may be positioned prior to the sensor wire 102 being positioned on the PCB 104. The rigid member 110 may be positioned on the PCB 104 such that the connection point 112 is located between the rigid member 110 and the PCB 104.

In block 406, a force is applied on the rigid member 110 to bond the rigid member 110 to the PCB 104. For example, the force may be applied by the robotic placement device to the contact surface 200 in the direction of the PCB 104. The suction head may maintain the vacuum seal on the contact surface 200 as the force is applied to maintain the connection between the robotic placement device and the rigid member 110. The force applied by the robotic placement device may activate the pressure-sensitive adhesive 204 between the rigid member 110 and the PCB 104 to bond the rigid member 110 to the PCB 104. In some aspects, the rigid member 110 includes the adhesive 204 on the coupling surface 202 prior to the rigid member 110 and the sensor wire 102 being positioned on the PCB 104 as described in block 404. In additional and alternative aspects, the rigid member includes the adhesive 204 or additional adhesive on the PCB 104 prior to the rigid member 110 and the sensor wire 102 being positioned on the PCB 104. Upon adhering the rigid member 110 and the sensor wire 102 to the PCT 104, the force may be removed from the contact surface 200. In some aspects, the force is removed simultaneously with a release of the vacuum seal created on the contact surface 200 as described in block 402.

In some aspects, the rigid member 110 is potted to the PCB 104. For example, a potting material may be applied on and around the rigid member 110 to create a moisture barrier for the connection point 112 located between the rigid member 110 and the PCB 104. Subsequent to any additional electronic components being connected to the PCB 104, the PCB 104 including the sensor wire 102 and the rigid member 110 may be disposed in the housing 116 to complete the biosensor 100's assembly.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. A method of assembling a biosensor, comprising:
receiving a sensor wire and a rigid member, the sensor wire including a distal end for insertion into a patient's skin and a proximal end attached to the rigid member;
creating, by a suction head of a robotic placement device, a vacuum seal on a smooth surface of the rigid member for grasping the rigid member;
positioning, by the robotic placement device and using the vacuum seal, the sensor wire and the rigid member on a printed circuit board with the sensor wire positioned between the rigid member and the printed circuit board; and
applying, by the robotic placement device, a force on the rigid member in a direction of the printed circuit board to cause a pressure-sensitive adhesive disposed on the rigid member to adhere the rigid member to the printed circuit board.

2. The method of claim 1, further comprising:
coupling, at a connection point on the printed circuit board, the sensor wire to circuitry disposed on the printed circuit board,
wherein positioning the sensor wire and the rigid member on the printed circuit board includes:
positioning the proximal end of the sensor wire on the printed circuit board at the connection point; and
positioning the rigid member on the printed circuit board such that the connection point is between a section of the printed circuit board and the rigid member.

3. The method of claim 1, further comprising:
applying a potting material proximate to the rigid member to create a moisture barrier at a connection point on the printed circuit board for the sensor wire and circuitry disposed on the printed circuit board.

4. The method of claim 1, further comprising disposing the printed circuit board within a housing of a wearable monitoring device, the housing having a substantially planar surface for positioning the wearable monitoring device on the patient's skin.

5. The method of claim 1, further comprising disposing a reactive material on the distal end of the sensor wire to react with glucose present in interstitial fluid beneath the patient's skin.

6. The method of claim 1, further comprising attaching the sensor wire to the rigid member prior to said receiving.

7. A device for a biosensor, comprising:
a sensor wire; and
a rigid member including a coupling surface that is attached to a proximal end of the sensor wire and is configured to couple to a printed circuit board of the biosensor, the rigid member further including a contact surface on an opposing side of the coupling surface, the contact surface sized to enable a suction head of a robotic placement device to create a vacuum seal on the contact surface.

8. The device of claim 7, wherein the coupling surface comprises an adhesive for coupling the rigid member to the printed circuit board of the biosensor.

9. The device of claim 8, wherein the adhesive is a pressure-sensitive adhesive.

10. The device of claim 8, wherein the sensor wire includes one or more electrodes, wherein the rigid member is oriented on the printed circuit board to electrically couple the one or more electrodes to circuitry disposed on the printed circuit board.

11. The device of claim 8, wherein the rigid member is positioned on the printed circuit board such that the proximal end of the sensor wire is between the printed circuit board and the coupling surface of the rigid member.

12. The device of claim 7, wherein the sensor wire further includes a distal end, wherein the proximal end is coupled to the rigid member and the distal end is insertable into a patient's skin to measure a glucose level of the patient.

13. The device of claim 7, wherein the sensor wire has a maximum outer diameter substantially between 100 microns and 300 microns.

14. The device of claim 7, wherein the sensor wire includes a length substantially between 5 millimeters and 25 millimeters.

15. The device of claim 7, wherein the contact surface of the rigid member has a length or diameter substantially between 1 millimeter and 10 millimeters.

16. A wearable monitoring device, comprising:
a printed circuit board disposed in a housing having a planar surface for positioning the wearable monitoring device on a patient's skin;
a sensor wire including one or more electrodes electrically coupled, at a connection point on the printed circuit board, to circuitry disposed on the printed circuit board, the sensor wire having a distal end that is insertable into the patient's skin; and
a rigid member coupled to the printed circuit board and the sensor wire with the sensor wire being positioned between the rigid member and the printed circuit board, the rigid member being positioned on the printed circuit board such that the connection point is between a section of the printed circuit board and a coupling surface of the rigid member, wherein the rigid member includes a contact surface opposite the coupling surface, the contact surface sized to enable a suction head of a robotic placement device to create a vacuum seal on the contact surface.

17. The wearable monitoring device of claim 16, wherein the rigid member comprises a non-conductive material to electrically isolate the sensor wire at the connection point.

18. The wearable monitoring device of claim 16, further including a potting material disposed on the rigid member to create a moisture barrier proximate to the connection point.

19. The wearable monitoring device of claim 16, wherein the rigid member is coupled to the printed circuit board by a pressure-sensitive adhesive.

20. The wearable monitoring device of claim 16, wherein the rigid member has a quadrilateral shape with at least one side having a length substantially between 1 millimeter and 10 millimeters.

21. The wearable monitoring device of claim 16, wherein the sensor wire includes a length that is at least twice as long as a length of the rigid member.

22. The wearable monitoring device of claim 16, wherein the one or more electrodes includes a first electrode comprising a platinum material and a second electrode comprising a silver/silver-chloride material.

23. The wearable monitoring device of claim 16, further comprising a glucose oxidase material disposed on the distal end of the sensor wire to react to glucose present within interstitial fluid beneath the patient's skin and enable the circuitry to determine an amount of the glucose present within the interstitial fluid.

\* \* \* \* \*